US006818432B2

(12) United States Patent
Farwick et al.

(10) Patent No.: US 6,818,432 B2
(45) Date of Patent: Nov. 16, 2004

(54) NUCLEOTIDE SEQUENCES ENCODING THE PTSH GENE

(75) Inventors: Mike Farwick, Bielefeld (DE); Bettina Mockel, Bielefeld (DE); Walter Pfefferle, Halle (DE)

(73) Assignee: Degussa AG, Dusseldorf (DE)

( * ) Notice: Subject to any disclaimer, the term of this patent is extended or adjusted under 35 U.S.C. 154(b) by 57 days.

(21) Appl. No.: 09/819,930

(22) Filed: Mar. 29, 2001

(65) Prior Publication Data

US 2003/0224499 A9 Dec. 4, 2003

Related U.S. Application Data

(63) Continuation-in-part of application No. 09/755,187, filed on Jan. 8, 2001, which is a continuation-in-part of application No. 09/503,189, filed on Feb. 14, 2000, now abandoned.

(30) Foreign Application Priority Data

Jan. 13, 2000  (DE) ......................................... 100 01 101

(51) Int. Cl.$^7$ ................................................ C12N 1/20
(52) U.S. Cl. .............. 435/252.3; 435/69.1; 435/252.32; 435/320.1; 536/23.2
(58) Field of Search ........................... 435/69.1, 252.3, 435/252.32, 320.1; 536/23.2; 530/350

(56) References Cited

FOREIGN PATENT DOCUMENTS

| EP | 0 197 335 | 10/1986 |
|---|---|---|
| WO | WO 96 34961 | 11/1996 |
| WO | WO 01 02583 | 1/2001 |

OTHER PUBLICATIONS

Ponting, C.P. Issues in predicting protein function from sequence. Brief. Bioinform. Mar. 2001, vol. 2(1), pp. 19–29.*
Attwood et al. Which craft is best in bioinformatics? Comput. Chem. 2001, vol. 25(4), pp. 329–339.*
Eiglmeier et al. GenBank Accession AL023591. Aug. 27, 1999.*
Quax, WJ. Accession AAX29477. Jun. 10, 1999.*
Charbit et al., "Function of the Duplicated IIB Domain and Oligomeric Structure of the Fructose Permease of *Escherichia Coli*," *Journal of Biological Chemistry*, vol. 271, No. 17, Apr. 26, 1996, pp. 9997–10003.
De Reuse et al., "The ptsH, ptsI, and crr Genes of the *Escherichia coli* Phosphoenolpyruvate–Dependent Phosphotransferase System: a Complex Operon with Several Modes of Transcription," *Journal of Bacteriology*, vol. 170, No. 9, Sep. 1988, pp. 3827–3837.
Deutscher et al., "Purification and Characterization of an ATP–Dependent Protein Kinase from *Streptococcus faecalis,*" *FEMS Microbiology Letters*, vol. 23, 1984, pp. 157–162.

Francke et al., "Flux Control of the Bacterial Phosphoenolpyruvate:Glucose Phosphotransferase System and the Effect of Diffusion," *Free University*.
Galinier et al., "The *Bacillus subtilis* crh Gene Encodes a HPr–Like Protein Involved in Carbon Catabolite Repression," *Proc. National Academy of Science*, vol. 94, Aug. 1997, pp. 8439–8444.
Herzberg et al., "Unraveling a Bacterial Hexose Transport Pathway," *Current Opinion in Structural Biology*, vol. 4, 1994, pp. 814–822.
Liao et al., "The First Step in Sugar Transport: Crystal Structure of the Amino Terminal Domain of Enzyme 1 of the *E. coli* PEP: Sugar Phosphotransferase System and a Model of the Phosphotransfer Complex with HPr," *Structure*, vol. 4, Jul. 15, 1996, pp. 861–872.
Reizer et al., "Properties of ATP–Dependent Protein Kinase from *Streptococcus pyogenes* That Phosphorylates a Seryl Residue in HPr, a Phosphocarrier Protein of the Phosphotransferase System," *Journal of Bacteriology*, vol. 160, No. 1, Oct. 1984, pp. 333–340.
Welch et al., "Extensive Mosaic Structure Revealed by the Complete Genome Sequence of Uropathogenic *Escherichia coli,*" *PNAS*, vol. 99, No. 26, Dec. 24, 2002, pp. 17020–17024.
Palmer et al., "*Pseudomonas putida* lipoamide dehydrogenase (IpdG) gene, complete cds", XP002169744, Database EMBL Accession No. M80189; M38421, Sep. 1991.
Parche Stephan et al., "The phosphotransferase system (PTS) of *Streptomyces coelicolor*: Identification and biochemical analysis of a histidine phosphocarrier protein HPr encoded by the gene ptsH.", European Journal of Biochemistry, vol. 265, Nr. 1, 1999, p. 308–317.
Lee et al., "Nucleotide sequence of the gene encoding the *Corynebacterium glutamicum* mannose enxyme II and analyses of the deduced protein sequence", FEMS Microbiology Letters, vol. 119, Nr. 1–2, 1994, p. 137–146.

* cited by examiner

Primary Examiner—Tekchand Saidha
Assistant Examiner—Christian L. Fronda
(74) *Attorney, Agent, or Firm*—Pillsbury Winthrop LLP (57) ABSTRACT

The invention relates to an isolated polynucleotide containing a polynucleotide sequence selected from the group comprising
  a) polynucleotide which is at least 70% identical to a polynucleotide which codes for a polypeptide containing the amino acid sequence of SEQ ID no. 2,
  b) polynucleotide which codes for a polypeptide containing an amino acid sequence which is at least 70% identical to the amino acid sequence of SEQ ID no.2,
  c) polynucleotide which is complementary to the polynucleotides of a) or b), and
  d) polynucleotide containing at least 15 successive nucleotides of the polynucleotide sequence of a), b) or c),
and a process for the fermentative production of L-amino acids with enhancement of the ptsH gene coding for component H of the phosphotransferase system, and the use of the above polynucleotides as primer or hybridisation probe.

8 Claims, 3 Drawing Sheets

Figure 1: Map of the plasmid pCRB1-ptsHexp

Figure 2: Plasmid pEC-K18mob2

Figure 3: Plasmid pEC-K18mob2ptsHexp

NUCLEOTIDE SEQUENCES ENCODING THE PTSH GENE

CROSS-REFERENCE TO RELATED APPLICATIONS

This is a continuation-in-part of U.S. patent application Ser. No. 09/755,187, filed Jan. 8, 2001, which itself is a continuation-in-part of U.S. patent application Ser. No. 09/503,189, filed on Feb. 14, 2000 now abandoned, which claims priority to German Patent Appl. No. DE 100 01 101.2, filed on Jan. 13, 2000.

BACKGROUND OF THE INVENTION

1. Field of the Invention

The present invention provides nucleotide sequences coding for ptsH and processes for the fermentative preparation of L-amino acids, particularly L-lysine, in which the ptsH gene is enhanced, using coryneform bacteria.

2. Background Information

L-amino acids, particularly L-lysine, are used in human medicine and in the pharmaceutical industry, and particularly in animal nutrition.

It is known to prepare L-amino acids by fermentation of strains of coryneform bacteria, particularly *Corynebacterium glutamicum*. In view of the great importance, work is constantly being carried out to improve the preparation processes. Process improvements may relate to measures involving the fermentation technique, such as, e.g., agitation and oxygen supply, or the composition of the nutrient media such as, e.g., the sugar concentration during fermentation, or the work up to the product form by, e.g., ion exchange chromatography, or the intrinsic performance properties of the microorganism itself.

In order to improve the performance properties of said microorganisms, methods of mutagenesis, selection and mutant selection are employed. Strains thereby obtained are resistant to antimetabolites such as, e.g., the lysine analogue S-(2-aminoethyl) cysteine, or auxotrophic for metabolites of regulatory importance and produce L-lysine.

For some years, methods of recombinant DNA technology have also been used to improve strains of coryneform bacteria producing L-amino acids by amplifying individual biosynthesis genes for L-amino acids and examining the effect on L-amino acid production. Review articles on this subject may be found inter alia in Kinoshita ("Glutamic Acid Bacteria", in: Biology of Industrial Microorganisms, Demain and Solomon (Eds.), Benjamin Cummings, London, UK, 1985, 115–142), Hilliger (BioTec 2, 40–44 (1991)), Eggeling (Amino Acids 6:261–272 (1994)), Jetten and Sinskey (Critical Reviews in Biotechnology 15, 73–103 (1995)) and Sahm et al. (Annuals of the New York Academy of Science 782, 25–39 (1996)).

SUMMARY OF THE INVENTION

Object of the Invention

The inventors set themselves the task of providing new measures for the improved fermentative preparation of L-amino acids, particularly L-lysine.

DESCRIPTION OF THE INVENTION

L-amino acids, particularly L-lysine, are used in human medicine, in the pharmaceutical industry and particularly in animal nutrition. It is of general interest, therefore, to provide new improved processes for the preparation of L-amino acids, particularly L-lysine.

Where the terms L-lysine or lysine are mentioned below, they refer not only to the base but also to the salts such as, e.g., lysine monohydrochloride or lysine sulfate.

The invention provides an isolated polynucleotide from coryneform bacteria containing a polynucleotide sequence selected from the group comprising a) polynucleotide which is at least 70% identical to a polynucleotide coding for a polypeptide which contains the amino acid sequence of SEQ ID no. 2, b) polynucleotide which codes for a polypeptide containing an amino acid sequence which is at least 70% identical to the amino acid sequence of SEQ ID no.2, c) polynucleotide which is complementary to the polynucleotides of a) or b), and d) polynucleotide containing at least 15 successive nucleotides of the polynucleotide sequence of a), b) or c).

The invention also provides a polynucleotide which is a DNA, preferably recombinant, which can be replicated in coryneform bacteria.

The invention also provides a polynucleotide which is an RNA.

The invention also provides a polynucleotide which is preferably a replicable DNA containing:

(i) the nucleotide sequence shown in SEQ ID no.1, or (ii) at least one sequence which corresponds to the sequence (i) within the degeneracy region of the genetic code, or (iii) at least one sequence which hybridises with the sequence complementary to sequence (i) or (ii), and optionally (iv) functionally neutral sense mutations in (i).

The invention also provides a vector containing one of the polynucleotides mentioned, and coryneform bacteria acting as host cell which contain the vector.

The invention also provides polynucleotides comprising substantially a polynucleotide sequence which may be obtained by screening by hybridising an appropriate gene bank containing the complete gene with the polynucleotide sequence corresponding to SEQ ID no. 1, with a probe which contains the sequence of the above-mentioned polynucleotide according to SEQ ID no. 1 or a fragment thereof, and isolating the DNA sequence mentioned.

Polynucleotide sequences according to the invention are suitable as hybridisation probes for RNA, cDNA and DNA, for isolating full-length cDNA which code for component H of the phosphotransferase system (ptsH) and for isolating those cDNA or genes which have great similarity of sequence with that of the gene for component H of the phosphotransferase system.

Polynucleotide sequences according to the invention are also suitable as primers for the preparation of DNA of genes which code for component H of the phosphotransferase system by the polymerase chain reaction (PCR).

The oligonucleotides acting as probes or primers contain at least 30, preferably at least 20, more particularly preferably at least 15 successive nucleotides. Oligonucleotides with a length of at least 40 or 50 nucleotides are also suitable.

"Isolated" means separated from its natural surroundings.

"Polynucleotide" refers generally to polyribonucleotides and polydeoxyribonucleotides, which may be unmodified RNA or DNA or modified RNA or DNA.

The term "polypeptides" means peptides or proteins which contain two or more amino acids bound by way of peptide bonds.

The polypeptides according to the invention include a polypeptide according to SEQ ID no. 2, and also those with the biological activity of component H of the phosphotransferase system and also those which are at least 70% identical to the polypeptide according to SEQ ID no. 2, preferably at least 80% and in particular those which are 90% to 95% identical to the polypeptide according to SEQ ID no. 2 and have the activity mentioned.

The invention also relates to a process for the fermentative preparation of L-amino acids, particularly L-lysine, using coryneform bacteria which in particular already produce an L-amino acid and in which the nucleotide sequences coding for the ptsH gene are enhanced, particularly overexpressed.

The term "enhancement" describes in this context the increase in intracellular activity of one or more enzymes in a microorganism which are coded for by the corresponding DNA, by, for example, increasing the copy number of the gene or genes or alleles, using a strong promotor or using a gene or allele which codes for a corresponding enzyme with a high activity and optionally combining said measures.

The microorganisms which are the subject of the present invention may produce L-amino acids, particularly L-lysine from glucose, sucrose, lactose, fructose, maltose, molasses, starch, cellulose or from glycerol and ethanol. They may be representatives of coryneform bacteria, particularly of the Corynebacterium genus. A particular example of the Corynebacterium genus is the *Corynebacterium glutamicum* type which is known by experts to have the ability to produce L-amino acids.

Examples of suitable strains of the Corynebacterium genus, particularly of the *Corynebacterium glutamicum* type include the well known wild-type strains

*Corynebacterium glutamicum* ATCC13032

*Corynebacterium acetoglutamicum* ATCC15806

*Corynebacterium acetoacidophilum* ATCC13870

*Corynebacterium thermoaminogenes* FERM BP-1539

*Corynebacterium melassecola* ATCC17965

*Brevibacterium flavum* ATCC14067

*Brevibacterium lactofermentum* ATCC13869 and

*Brevibacterium divaricatum* ATCC14020 and L-lysine-producing mutants and strains prepared therefrom, such as, for example

*Corynebacterium glutamicum* FERM-P 1709

*Brevibacterium flavum* FERM-P 1708

*Brevibacterium lactofermentum* FERM-P 1712

*Corynebacterium glutamicum* FERM-P 6463

*Corynebacterium glutamicum* FERM-P 6464 and

*Corynebacterium glutamicum* DSM5715.

The inventors succeeded in isolating from *C. glutamicum* the new ptsH gene coding for component H of the phosphotransferase system.

In order to isolate the ptsH gene or other genes from *C. glutamicum*, a gene bank of this microorganism is first prepared in *E. coli*. The preparation of gene banks is documented in generally known textbooks and manuals. Examples include the textbook by Winnacker: Gene und Klone, Eine Einführung in die Gentechnologie (Verlag Chemie, Weinheim, Germany, 1990) or the manual by Sambrook et al.: Molecular Cloning, A Laboratory Manual (Cold Spring Harbor Laboratory Press, 1989). A very well known gene bank is that of the *E. coli* K-12 strain W3110, which was prepared by von Kohara et al. (Cell 50, 495–508 (1987)) in λ-vectors. Bathe et al. (Molecular and General Genetics, 252:255–265, 1996) describe a gene bank of *C. glutamicum* ATCC13032 which was prepared using the cosmid vector SuperCos I (Wahl et al., 1987, Proceedings of the National Academy of Sciences USA, 84:2160–2164) in the *E. coli* K-12 strain NM554 (Raleigh et al., 1988, Nucleic Acids Research 16:1563–1575). Börmann et al. (Molecular Microbiology 6(3), 317–326 (1992)) in turn describe a gene bank of *C. glutamicum* ATCC13032 using the cosmid pHC79 (Hohn and Collins, Gene 11, 291–298 (1980)). In order to prepare a gene bank of *C. glutamicum* in *E. coli*, it is also possible to use plasmids such as pBR322 (Bolivar, Life Sciences, 25, 807–818 (1979)) or pUC9 (Vieira et al., 1982, Gene, 19:259–268). Particularly suitable hosts are *E. coli* strains which are restriction- and recombination-defective. An example of these is the DH5αMCR strain which was described by Grant et al. (Proceedings of the National Academy of Sciences USA, 87 (1990) 4645–4649). The long DNA fragments cloned using cosmids may then in turn be subcloned into common vectors suitable for sequencing, and then sequenced, as described in Sanger et al. (Proceedings of the National Academy of Sciences of the United States of America, 74:5463–5467, 1977).

The new DNA sequence coding for ptsH was obtained in this way from *C. glutamicum* and, as SEQ ID no. 1, forms part of the present invention. Moreover, the amino acid sequence of the corresponding protein was derived from the present DNA sequence with the methods described above. The resulting amino acid sequence of the ptsH gene product is shown in SEQ ID no. 2.

Coding DNA sequences resulting from SEQ ID No. 1 due to the degeneracy of the genetic code also form part of the invention. Experts are also familiar with conservative amino acid exchanges such as, e.g., the exchange of glycine for alanine or of aspartic acid for glutamic acid in proteins as "sense mutations" which do not lead to a fundamental change in the activity of the protein, i.e. which are functionally neutral. It is also known that changes at the N and/or C end of a protein do not substantially impair or may even stabilise its function. Experts may find details on this subject, inter alia, in Ben-Bassat et al. (Journal of Bacteriology 169:751–757 (1987)), in O'Regan et al. (Gene 77:237–251 (1989)), in Sahin-Toth et al. (Protein Sciences 3:240–247 (1994)), in Hochuli et al. (Bio/Technology 6:1321–1325 (1988)) and in well known textbooks of genetics and molecular biology. Amino acid sequences which are obtained in corresponding manner from SEQ ID no. 2 and these DNA sequences encoding amino acid sequences also form part of the invention.

Similarly, DNA sequences which hybridise with SEQ ID no. 1 or parts of SEQ ID no. 1 form part of the invention. Finally, DNA sequences which are prepared by the polymerase chain reaction (PCR) using primers obtained from SEQ ID no. 1 form part of the invention. Such oligonucleotides typically have a length of at least 15 nucleotides.

The expert may find instructions for the identification of DNA sequences by hybridisation inter alia in the manual "The DIG System Users Guide for Filter Hybridization" from Firma Boehringer Mannheim GmbH (Mannheim, Germany, 1993) and in Liebl et al. (International Journal of Systematic Bacteriology (1991) 41:255–260). The expert may find instructions for the amplification of DNA sequences using the polymerase chain reaction (PCR) inter alia in the manual by Gait: Oligonucleotide synthesis: a practical approach (IRL Press, Oxford, UK, 1984) and in Newton and Graham: PCR (Spektrum Akademischer Verlag, Heidelberg, Germany, 1994).

The inventors discovered that coryneform bacteria produce L-amino acids, particularly L-lysine, in an improved manner after overexpression of the ptsH gene.

In order to obtain overexpression, the copy number of the corresponding gene may be increased, or the promotor and regulatory region or the ribosome binding site situated upstream of the structural gene may be mutated. Expression cassettes which are incorporated upstream of the structural gene act in the same way. As a result of inducible promoters, it is also possible to increase expression in the course of fermentative L-amino acid production. Expression is also improved by measures to prolong the life of the m-RNA. Moreover, by preventing the degradation of the enzyme protein, the enzyme activity is also increased. The genes or gene constructs may either be present in plasmids with a different copy number, or integrated in the chromosome and amplified. Alternatively, overexpression of the genes concerned may be achieved by altering the composition of the medium and the way in which the culture is carried out.

The expert may find instructions on this subject inter alia in Martin et al. (Bio/Technology 5, 137–146 (1987)), in Guerrero et al. (Gene 138, 35–41 (1994)), Tsuchiya and Morinaga (Bio/Technology 6, 428–430 (1988)), in Eikmanns et al. (Gene 102, 93–98 (1991)), in the European patent EPS 0 472 869, in U.S. Pat. No. 4,601,893, in Schwarzer and Pühler (Bio/Technology 9, 84–87 (1991), in Reinscheid et al. (Applied and Environmental Microbiology 60, 126–132 (1994)), in LaBarre et al. (Journal of Bacteriology 175, 1001–1007 (1993)), in the patent application WO 96/15246, in Malumbres et al. (Gene 134, 15–24 (1993)), in the Japanese specification JP-A-10-229891, in Jensen and Hammer (Biotechnology and Bioengineering 58, 191–195 (1998)), in Makrides (Microbiological Reviews 60:512–538 (1996)) and in well known textbooks of genetics and molecular biology.

By way of example, the ptsH gene according to the invention was overexpressed using plasmids.

Suitable plasmids are those which are replicated in coryneform bacteria. Numerous well known plasmid vectors such as, e.g., pZ1 (Menkel et al., Applied and Environmental Microbiology (1989) 64:549–554), pEKEx1 (Eikmanns et al., Gene 102:93–98 (1991)) or pHS2-1 (Sonnen et al., Gene 107:69–74 (1991)) are based on the cryptic plasmids pHM1519, pBL1 or pGA1. Other plasmid vectors such as, e.g., those based on pCG4 (U.S. Pat. No. 4,489,160) or pNG2 (Serwold-Davis et al., FEMS Microbiology Letters 66, 119–124 (1990)) or pAG1 (US-A 5,158,891) may be used in the same way.

Other suitable plasmid vectors include those by means of which the process of gene amplification by integration into the chromosome may be employed, as was described, e.g., by Reinscheid et al. (Applied and Environmental Microbiology 60, 126–132 (1994)) for the duplication and amplification of the hom-thrB operon. In this method, the complete gene is cloned into a plasmid vector which is able to replicate in a host (typically *E. coli*), but not in *C. glutamicum*. Examples of suitable vectors include pSUP301 (Simon et al., Bio/Technology 1, 784–791 (1983)), pK18mob or pK19mob (Schäfer et al., Gene 145, 69–73 (1994)), pGEM-T (Promega corporation, Madison, Wis., USA), pCR2.1-TOPO (Shuman (1994). Journal of Biological Chemistry 269:32678–84; U.S. Pat. No. 5,487,993), pCR®Blunt (Firma Invitrogen, Groningen, Niederlande; Bernard et al., Journal of Molecular Biology, 234:534–541 (1993)) or pEM1 (Schrumpf et al, 1991, Journal of Bacteriology 173:4510–4516). The plasmid vector which contains the gene to be amplified is then transferred by conjugation or transformation into the desired strain of *C. glutamicum*. The conjugation method is described, for example, in Sch äfer et al. (Applied and Environmental Microbiology 60, 756–759 (1994)). Methods of transformation are described, for example, in Thierbach et al. (Applied Microbiology and Biotechnology 29, 356–362 (1988)), Dunican and Shivnan (Bio/Technology 7, 1067–1070 (1989)) and Tauch et al. (FEMS Microbiological Letters 123, 343–347 (1994)). After homologous recombination using a "cross over" event, the resulting strain contains at least two copies of the gene concerned.

The invention also provides, therefore, a process for the fermentative preparation of L-amino acids, particularly L-lysine, wherein a strain transformed with a plasmid vector is used and the plasmid vector carries the nucleotide sequence of the gene coding for component H of the phosphotransferase system.

Moreover, it was found that by exchanging the amino acid L-alanine in position 25 of the protein component H of the phosphotransferase system (see SEQ ID NO:2) for any other proteinogenic amino acid, particularly L-threonine (see SEQ ID NO:4), with the exception of L-alanine, enhancement takes place and coryneform bacteria which bear the corresponding amino acid exchange produce L-lysine in an improved manner. The exchange of L-alanine for L-threonine in position 25 of the amino acid sequence may be carried out preferably by exchanging the nucleobase adenine in position 235 for guanine, as shown in the nucleotide sequence according to SEQ ID NO:3.

Conventional mutagenesis methods using mutagenic substances such as, for example, N-methyl-N'-nitro-N-nitrosoguanidine or ultraviolet light may be used for mutagenesis. Moreover, in vitro methods such as, for example, a treatment with hydroxylamine or mutagenic oligonucleotides or the polymerase chain reaction (PCR) may be used for mutagenesis.

Accordingly, the invention also provides coryneform bacteria which contain a protein component H of the phosphotransferase system in which the amino acid sequence in position 25 shown under SEQ ID NO:2 is exchanged for another amino acid except L-alanine. A further aspect of this invention is coryneform bacteria which contain a corresponding protein in which the amino acid L-alanine in position 25 of the protein (see SEQ ID NO:2) is exchanged for L-threonine (see SEQ ID NO:4).

Accordingly, the invention also provides polynucleotide sequences originating from coryneform bacteria which contain genes or alleles which encode the above-mentioned protein components H of the phosphotransferase system.

The present invention also provides coryneform bacteria which contain a DNA encoding a protein component H of the phosphotransferase system which is characterised by the exchange of L-alanine for L-threonine in position 25, which DNA contains adenine instead of the nucleobase guanine in position 235 (see SEQ ID NO:1), as shown in SEQ ID NO:3.

In addition, it may be advantageous for the preparation of L-amino acids, particularly L-lysine, to enhance not only the ptsH gene but also other genes of the biosynthesis pathway of the desired L-amino acid so that one or more enzymes of the biosynthesis pathway in question, glycolysis, anaplerotic reactions or amino acid export, is overexpressed.

For the preparation of L-lysine, for example, it is possible to overexpress simultaneously one or more of the genes selected from the group comprising the dapA gene coding for dihydrodipicolinate synthase (EP-B 0 197 335), the gap gene coding for glyceraldehyde-3-phosphate dehydrogenase (Eikmanns (1992), Journal of Bacteriology 174:6076–6086), the tpi gene coding for triosephosphate isomerase (Eikmanns (1992), Journal of Bacteriology 174:6076–6086), the pgk gene coding for 3-phosphoglycerate kinase (Eikmanns (1992), Journal of Bacteriology 174:6076–6086), the ptsM gene coding for component M of the phosphoenolpyruvate-sugar-phosphotransferase system (ptsM) (Lee et al. (1994), FEMS Microbiology Letters 1–2, 137–145), the pyc gene coding for pyruvate carboxylase (DE-A-198 31 609), and the lysE gene coding for lysine export (DE-A-195 48 222).

Moreover, for the production of L-amino acids, particularly L-lysine, it may be advantageous, in addition to the ptsH gene, simultaneously to attenuate the pck gene coding for phosphoenolpyruvate carboxykinase (DE 199 50 409.1, DSM 13047) and/or the pgi gene coding for glucose-6-phosphate isomerase (U.S. Pat. No. 09/396,478, DSM 12969)

the poxB gene coding for pyruvate oxidase (DE 19846499.1; DSM 13114).

Moreover, for the production of L-amino acids, particularly L-lysine, it may be advantageous, in addition to the overexpression of the ptsH gene, to exclude unwanted side reactions (Nakayama: "Breeding of Amino Acid Producing Micro-organisms", in: Overproduction of Microbial Products, Krumphanzl, Sikyta, Vanek (eds.), Academic Press, London, UK, 1982).

The microorganisms produced according to the invention may be cultivated continuously or batchwise in the batch process (batch cultivation) or in the fed-batch or repeated fed-batch process in order to produce L-amino acids, particularly L-lysine. Summaries of well known cultivation methods are described in the textbook by Chmiel (Bioprozesstechnik 1. Einführung in die Bioverfahrenstechnik (Gustav Fischer Verlag, Stuttgart, 1991)) or in the textbook by Storhas (Bioreaktoren und periphere Einrichtungen (Vieweg Verlag, Braunschweig/Wiesbaden, 1994)).

The culture medium to be used must satisfy the requirements of the strains concerned in a suitable manner. Descriptions of culture media of various microorganisms are contained in the manual "Manual of Methods for General Bacteriology" of the American Society for Bacteriology (Washington D.C., USA, 1981). Suitable sources of carbon include sugars and carbohydrates such as, e.g., glucose, sucrose, lactose, fructose, maltose, molasses, starch and cellulose, oils and fats such as, e.g., soyabean oil, sunflower oil, groundnut oil and coconut fat, fatty acids such as, e.g., palmitic acid, stearic acid and linoleic acid, alcohols such as, e.g., glycerol and ethanol and organic acids such as, e.g., acetic acid. Said substances may be used individually or as mixtures. Suitable sources of nitrogen include organic nitrogen-containing compounds such as peptones, yeast extract, meat extract, malt extract, maize swelling water, soyabean flour and urea or inorganic compounds such as ammonium sulfate, ammonium chloride, ammonium phosphate, ammonium carbonate and ammonium nitrate. The sources of nitrogen may be used individually or as a mixture. Suitable sources of phosphorus include phosphoric acid, potassium dihydrogen phosphate or dipotassium hydrogen phosphate or the corresponding sodium-containing salts. The culture medium must also contain salts of metals such as, e.g., magnesium sulfate or iron sulfate which are necessary for growth. Finally, essential growth-promotors such as amino acids and vitamins may be used in addition to the substances mentioned above. Moreover, suitable preliminary stages may be added to the culture medium. The substances used may be added to the culture in the form of a single preparation or fed in a suitable manner during cultivation.

In order to control the pH of the culture, basic compounds such as sodium hydroxide, potassium hydroxide, ammonia or ammoniacal gas liquor or acid compounds such as phosphoric acid or sulfuric acid may be used in a suitable manner. Antifoaming agents such as, e.g., fatty acid polyglycol esters may be used to control foam development. In order to maintain the stability of plasmids, suitable selectively acting substances such as, e.g., antibiotics may be added to the medium. To maintain aerobic conditions, oxygen or oxygen-containing gas mixtures such as, e.g., air may be introduced into the culture. The temperature of the culture is normally from 20° C. to 45° C. and preferably from 25° C. to 40° C. The culture is continued until an L-lysine maximum has formed. This objective is normally achieved within 10 hours to 160 hours.

The invention also provides, therefore, a process for the fermentative preparation of L-amino acids, particularly L-lysine, wherein the following steps are carried out:

a) Fermentation of coryneform bacteria producing L-amino acids in which at least the ptsH gene coding for component H of the phosphotransferase system is enhanced, particularly overexpressed.

b) Enrichment of the L-amino acid in the medium or in the cells of the bacteria, and c) Isolation of the L-amino acid.

The analysis of L-lysine may be carried out by anion exchange chromatography followed by ninhydrin derivatisation, as described in Spackman et al. (Analytical Chemistry, 30, (1958), 1190).

The process according to the invention is used for the fermentative preparation of L-amino acids, particularly L-lysine.

DETAILED DESCRIPTION OF THE INVENTION

The present invention is explained in more detail below on the basis of embodiments.

EXAMPLE 1

Preparation of a Genomic Cosmid Gene Bank From *Corynebacterium glutamicum* ATCC 13032

Chromosomal DNA from *Corynebacterium glutamicum* ATCC 13032 was isolated as described in Tauch et al. (1995, Plasmid 33:168–179) and partially cleaved with the restriction enzyme Sau3AI (Amersham Pharmacia, Freiburg, Germany, product description Sau3AI, code no. 27-0913-02). The DNA fragments were dephosphorylated with Shrimp alkaline phosphatase (Roche Molecular Biochemicals, Mannheim, Germany, product description SAP, code no. 1758250). The DNA of the cosmid vector SuperCos1 (Wahl et al. (1987) Proceedings of the National Academy of Sciences USA 84:2160–2164), purchased from the company Stratagene (La Jolla, USA, product description SuperCos1 Cosmid Vector Kit, code no. 251301) was cleaved with the restriction enzyme XbaI (Amersham Pharmacia, Freiburg, Germany, product description XbaI, code no. 27-0948-02) and likewise dephosphorylated with Shrimp alkaline phosphatase. The cosmid DNA was then cleaved with the restriction enzyme BamHI (Amersham Pharmacia, Freiburg, Germany, product description BamHI, code no. 27-0868-04). The cosmid DNA treated in this way was mixed with the treated ATCC 13032-DNA and the batch was treated with T4-DNA-ligase (Amersham Pharmacia, Freiburg, Germany, product description T4-DNA-Ligase, code no.27-0870-04). The ligation mixture was then packaged into phages using Gigapack II XL Packing Extracts (Stratagene, La Jolla, USA, product description Gigapack II XL Packing Extract, code no. 200217). In order to infect the E. coli strain NM554 (Raleigh et al. 1988, Nucleic Acid Research 16:1563–1575) the cells were taken up in 10 mM $MgSO_4$ and mixed with an aliquot of the phage suspension. Infection and titration of the cosmid bank were carried out as described in Sambrook et al. (1989, Molecular Cloning: A Laboratory Manual, Cold Spring Harbor), the cells being plated on LB-Agar (Lennox, 1955, Virology, 1:190) with 100 μg/ml ampicillin. After incubation overnight at 37° C., recombinant individual clones were selected.

EXAMPLE 2
Isolation and Sequencing of the ptsH Gene

The cosmid DNA of an individual colony was isolated with the Qiaprep Spin Miniprep Kit (Product No. 27106, Qiagen, Hilden, Germany) in accordance with the manufacturer's instructions and partially cleaved with the restriction enzyme Sau3AI (Amersham Pharmacia, Freiburg, Germany, product description Sau3AI, product No. 27-0913-02). The DNA fragments were dephosphorylated with Shrimp alkaline phosphatase (Roche Molecular Biochemicals, Mannheim, Germany, product description SAP, product No. 1758250). After separation by gel electrophoresis, isolation of the cosmid fragments in the size region from 1500 to 2000 bp was carried out with the QiaExII Gel Extraction Kit (product No. 20021, Qiagen, Hilden, Germany). The DNA of the sequencing vector pZero-1 purchased from the company Invitrogen (Groningen, the Netherlands, product description Zero Background Cloning Kit, product No. K2500-01) was cleaved with the restriction enzyme BamHI (Amersham Pharmacia, Freiburg, Germany, product description BamHI, product No. 27-0868-04). Ligation of the cosmid fragments into the sequencing vector pZero-1 was carried out as described by Sambrook et al. (1989, Molecular Cloning: A laboratory Manual, Cold Spring Harbor), the DNA mixture being incubated overnight with T4-ligase (Pharmacia Biotech, Freiburg, Germany). This ligation mixture was then inserted in the E. coli strain DH5αMCR by microporation (Grant, 1990, Proceedings of the National Academy of Sciences U.S.A., 87:4645–4649) (Tauch et al. 1994, FEMS Microbiol Letters, 123:343–7) and plated on LB-agar (Lennox, 1955, Virology, 1:190) with 50 μg/ml Zeocin. Plasmid preparation of the recombinant clones was carried out with the Biorobot 9600 (Product No. 900200, Qiagen, Hilden, Germany). Sequencing was carried out by the dideoxy-chain termination method of Sanger et al. (1977, Proceedings of the National Academy of Sciences U.S.A., 74:5463–5467) with modifications after Zimmermann et al. (1990, Nucleic Acids Research, 18:1067). The "RR dRhodamin Terminator Cycle Sequencing Kit" from PE Applied Biosystems (product No. 403044, Weiterstadt, Germany) was used. Separation by gel electrophoresis and analysis of the sequencing reaction was carried out in a "Rotiphoresis NF acrylamide/bisacrylamide" gel (29:1) (product No. A124.1, Roth, Karlsruhe, Germany) with the "ABI Prism 377" sequencing device from PE Applied Biosystems (Weiterstadt, Germany).

The raw sequence data obtained were then processed using the Staden program package (1986, Nucleic Acids Research, 14:217–231) version 97-0. The individual sequences of the pZero1 derivatives were assembled to a coherent contig. The computer-controlled coding region analysis was prepared with the program XNIP (Staden, 1986, Nucleic Acids Research, 14:217–231). Further analyses were carried out with the "BLAST search programs" (Altschul et al., 1997, Nucleic Acids Research, 25:3389–3402), against the non-redundant data base of the "National Center for Biotechnology Information" (NCBI, Bethesda, Md., USA).

The nucleotide sequence obtained is shown in SEQ ID no. 1. The analysis of the nucleotide sequence revealed an open reading frame of 267 base pairs, which was designated the ptsH gene. The ptsH gene codes for a protein of 89 amino acids.

EXAMPLE 3
Preparation of a Shuttle Vector pEC-K18mob2ptsHexp in Order to Enhance the ptsH Gene in C. glutamicum
3.1 Cloning the ptsH Gene into the Vector pCR®Blunt II Chromosomal DNA was isolated from the ATCC 13032 strain according to the method of Eikmanns et al. (Microbiology 140:1817–1828 (1994)). On the basis of the sequence of the ptsH gene known from Example 2 for C. glutamicum, the following oligonucleotides were selected for the polymerase chain reaction:

```
PtsHexp1
5'-ACC ACT GGT GCA ATC TCC AT-3' (SEQ ID NO:5)

PtsHexp2
5'-TTT ACT CAG CGT CAA GGT CC 3' (SEQ ID NO:6)
```

The primers shown were synthesised by ARK Scientific GmbH Biosystems (Darmstadt, Germany) and the PCR reaction was carried out according to the standard PCR method of Innis et al. (PCR protocols. A Guide to Methods and Applications, 1990, Academic Press) with Pwo-polymerase from Roche Diagnostics GmbH (Mannheim, Germany). With the aid of the polymerase chain reaction, the primers permit the amplification of a 686 bp DNA fragment which bears the ptsH gene with the potential promotor region. The DNA sequence of the amplified DNA fragment was analysed by sequencing.

The amplified DNA fragment was ligated with the Zero Blunt™ Kit from Invitrogen Corporation (Carlsbad, Calif., USA; catalogue number K2700-20) into the vector pCR®Blunt II (Bernard et al., Journal of Molecular Biology, 234:534–541 (1993)).

Figure 1:
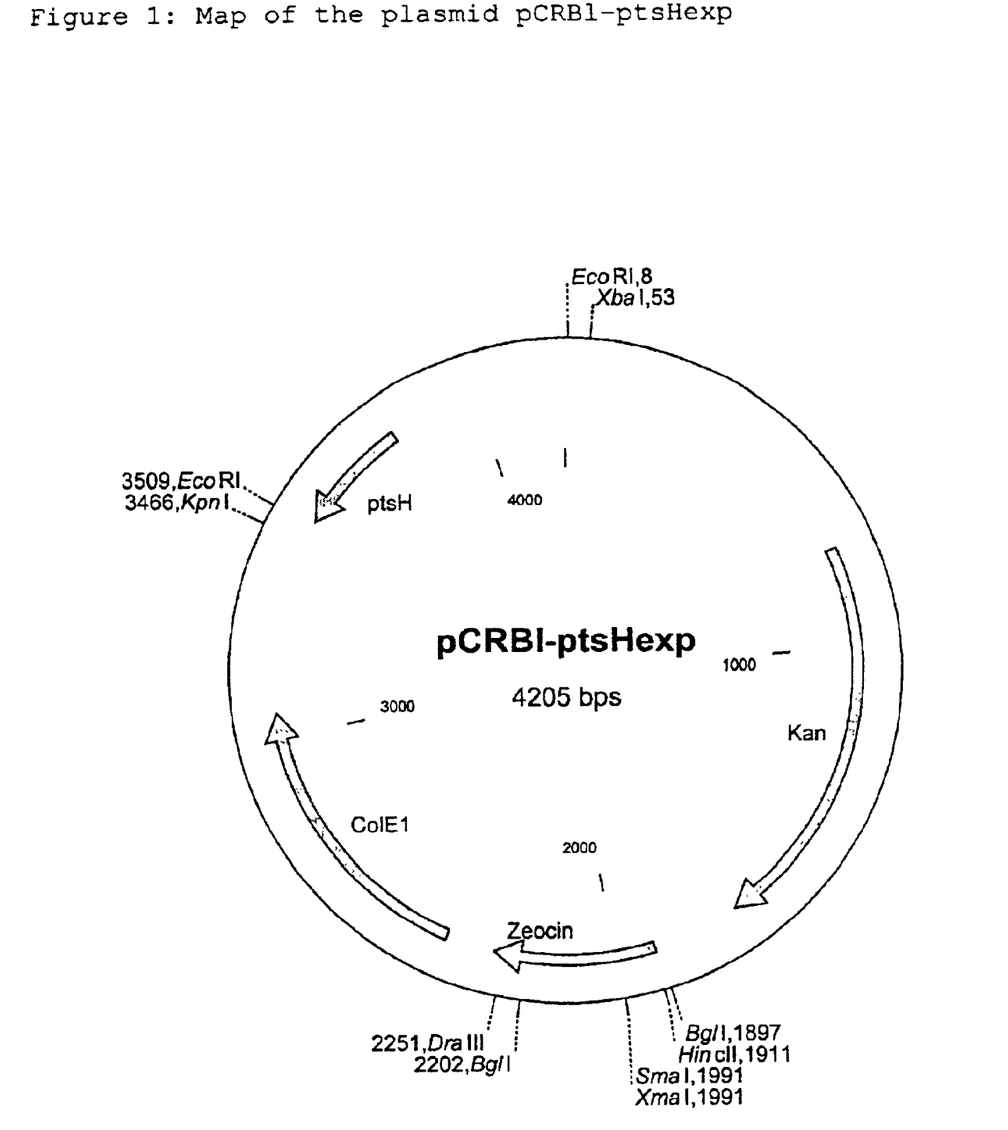
FIG. 1: Map of plasmid pCRB1-ptsHexp

The E. coli strain TOP10 was then electroporated with the ligation mix (Hanahan, In: DNA Cloning. A Practical Approach. Vol. I., IRL-Press, Oxford, Washington D.C., USA, 1985). The plasmid-bearing cells were selected by plating the transformation mix onto LB agar (Sambrook et al., Molecular Cloning: A Laboratory Manual. 2nd ed., Cold Spring Harbor Laboratory Press, Cold Spring Harbor, N.Y., 1989) which had been supplemented with 25 mg/l of kanamycin. Plasmid DNA was isolated from a transformant using the QIAprep Spin Miniprep Kit from Qiagen and analysed by restriction with the restriction enzyme EcoRI followed by agarose gel electrophoresis (0.8%). The plasmid was named pCRB1-ptsHexp and is shown in FIG. 1.

3.2 Preparation of the E. coli—C. glutamicum Shuttle Vector pEC-K18mob2

Figure 2:
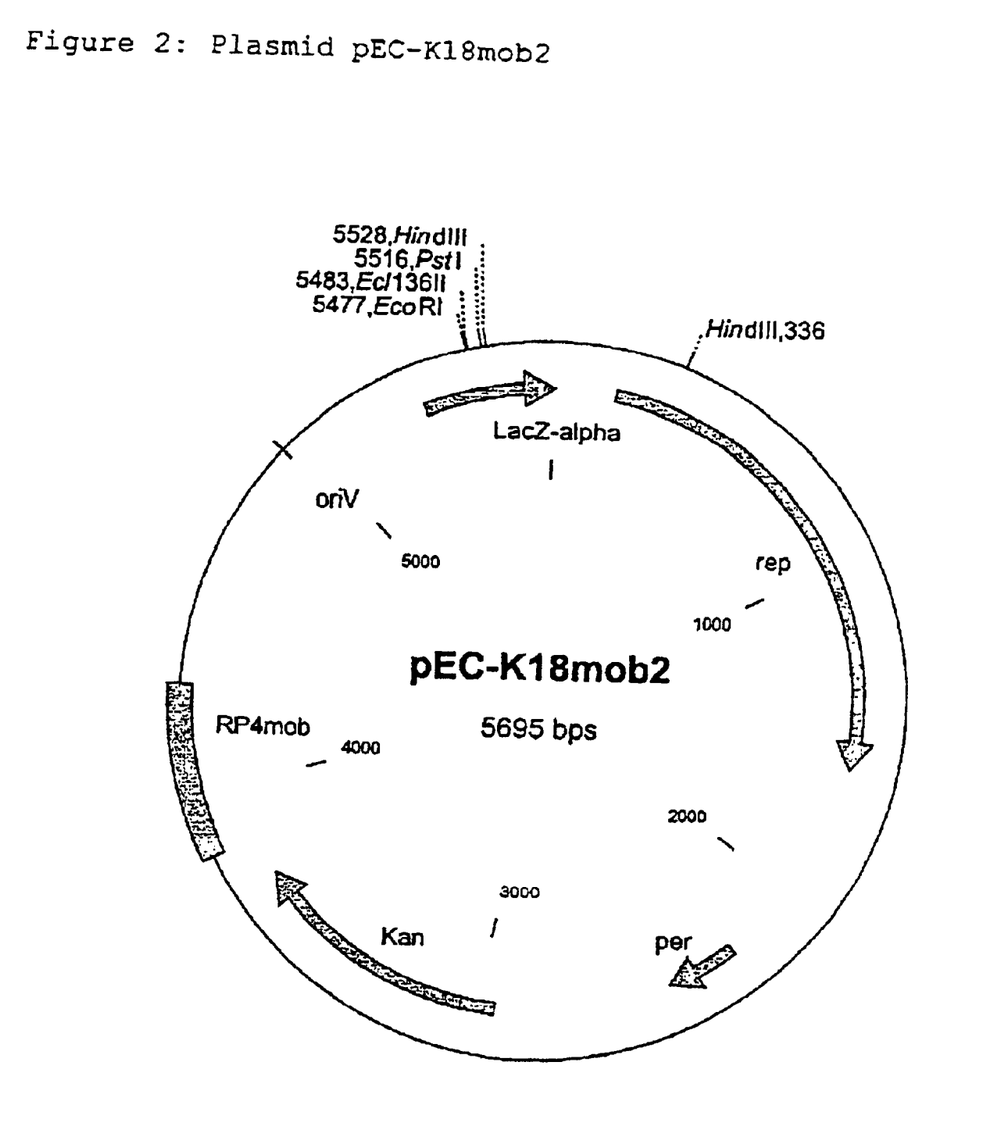
FIG. 2: Map of plasmid pEC-K18mob2

The E. coli—C. glutamicum shuttle vector was constructed according to the prior art. The vector contains the replication region rep of plasmid pGA1 including the replication effector per (U.S. Pat. No. 5,175,108; Nesvera et al., Journal of Bacteriology 179, 1525–1532 (1997)), the kanamycin resistance-conferring aph(3')-IIa gene of the transposon Tn5 (Beck et al., Gene 19, 327–336 (1982)), the replication region oriV of the plasmid pMB1 (Sutcliffe, Cold Spring Harbor Symposium on Quantitative Biology 43, 77–90 (1979)), the lacZα gene fragment including the lac promotor and a multiple cloning site (mcs) (Norrander, J. M. et al., Gene 26, 101–106 (1983)) and the mob region of plasmid RP4 (Simon et al., Biol/Technology 1:784–791 (1983)). The vector constructed was transformed into the E.

coli strain DH5αmcr (Hanahan, in: DNA Cloning. A Practical Approach. Vol. I, IRL-Press, Oxford, Washington D.C., USA). The plasmid-bearing cells were selected by plating the transformation mix onto LB agar (Sambrook et al., Molecular Cloning: A Laboratory Manual. 2nd ed., Cold Spring Harbor Laboratory Press, Cold Spring Harbor, N.Y.) which had been supplemented with 25 mg/l of kanamycin. Plasmid DNA was isolated from a transformant using the QIAprep Spin Miniprep Kit from Qiagen and analysed by restriction with the restriction enzyme EcoRI and HindIII followed by agarose gel electrophoresis (0.8%). The plasmid was named pEC-K18mob2 and is shown in FIG. 2.

The following microorganism was deposited at the German Collection for Microorganisms and Cell Cultures (DSMZ, Braunschweig, Germany) in accordance with the Budapest Agreement:

C. glutamicum strain DMS 5715/pEC-K18mob2 as DSM 13245

3.3 Cloning ptsH into the E. coli—C. glutamicum Shuttle Vector pEC-K18mob2

In order to clone the ptsH gene into the E. coli—C. glutamicum shuttle vector pEC-K18mob2 described in Example 3.2, plasmid DNA from pEC-K18mob2 was completely digested with the restriction endonucleases KpnI and XbaI and treated with alkaline phosphatase (Alkaline phosphatase, Roche Diagnostics GmbH, Mannheim, Germany).

Figure 3:
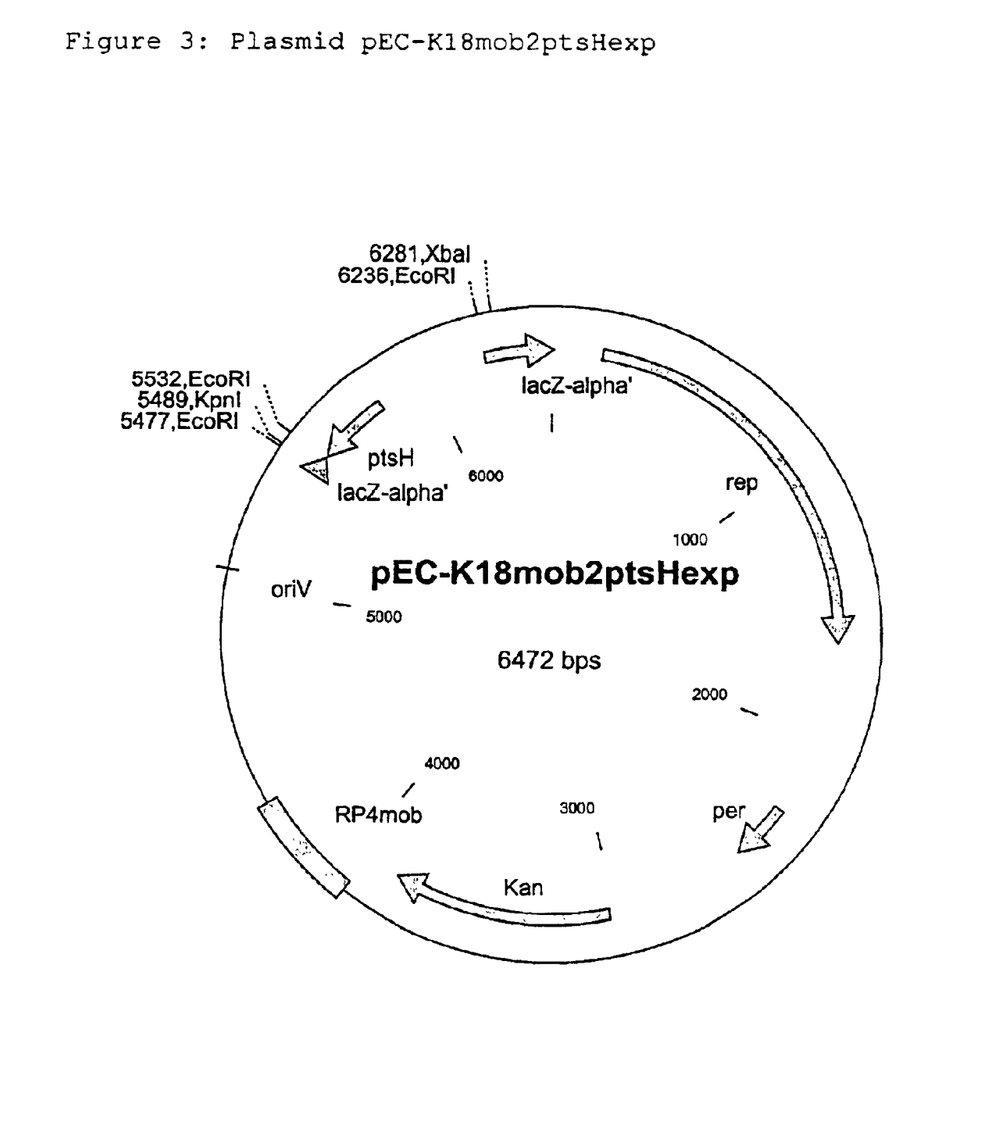
FIG. 3: Map of plasmid pEC-K18mob2ptsHexp

The vector pCRB1-ptsHexp was isolated from Escherichia coli Top10 and completely digested with the restriction endonucleases KpnI and XbaI, and the 788 bp fragment with the ptsH gene was purified from a 0.8% agarose gel (QIAquick Gel Extraction Kit from Qiagen, Hilden, Germany). The fragment with the ptsH gene was then ligated with the vector pEC-K18mob2 (T4-ligase, Roche Diagnostics GmbH, Mannheim; Germany). The ligation mix was transformed into the E. coli strain DH5αmcr (Hanahan, in: DNA Cloning. A Practical Approach. Vol. I. IRL-Press, Oxford, Washington D.C., USA). The plasmid-bearing cells were selected by plating the transformation mix onto LB agar (Sambrook et al., Molecular Cloning: A Laboratory Manual. 2nd ed., Cold Spring Harbor Laboratory Press, Cold Spring Harbor, N.Y., 1989) which had been supplemented with 25 mg/l of kanamycin. Plasmid DNA was isolated from a transformant using the QIAprep Spin Miniprep Kit from Qiagen (Hilden, Germany) and analysed by treatment with the restriction enzyme EcoRI followed by agarose gel electrophoresis. The plasmid was named pEC-K18mob2ptsHexp and is shown in FIG. 3.

The strain was named E. coli DH5αmcr/pEC-K18mob2ptsHexp and deposited in the form of a pure culture on Nov. 28, 2000 at the German Collection for Microorganisms and Cell Cultures (DSMZ, Braunschweig, Germany) as DSM 13878, in accordance with the Budapest Agreement.

EXAMPLE 4

Transformation of the Strain DSM5715 With Plasmid pEC-K18mob2ptsHexp

The strain DSM5715 was transformed with plasmid pEC-K18mob2ptsHexp using the electroporation method described by Liebl et al., (FEMS Microbiology Letters, 53:299–303 (1989)). The transformants were selected on LBHIS agar composed of 18.5 g/l brain-heart infusion broth, 0.5 M sorbitol, 5 g/l Bacto-trypton, 2.5 g/l Bacto-yeast extract, 5 g/l NaCl and 18 g/l Bacto-agar which had been supplemented with 25 mg/l kanamycin. Incubation took place for 2 days at 33° C.

Plasmid DNA was isolated from a transformant by the usual methods (Peters-Wendisch et al., 1998, Microbiology, 144, 915–927), cut with the restriction endonuclease EcoRI and the plasmid was then analysed by agarose gel electrophoresis. The strain obtained was named DSM5715/pEC-K18mob2ptsHexp.

EXAMPLE 5

Preparation of Lysine

The C. glutamicum strain DSM5715/pEC-K18mob2ptsHexp obtained in Example 4 was cultured in a nutrient medium suitable for the production of lysine, and the lysine content in the culture supernatant was determined.

To this end, the strain was initially incubated for 24 hours at 33° C. on an agar plate with the appropriate antibiotic (brain-heart agar with kanamycin (25 mg/l)). Starting from this agar plate culture, a pre-culture was inoculated (10 ml of medium in 100 ml Erlenmeyer flask). The medium used for the pre-culture was the solid medium Cg III.

| Cg III medium | |
|---|---|
| NaCl | 2.5 g/l |
| Bacto-peptone | 10 g/l |
| Bacto-yeast extract | 10 g/l |
| Glucose (autoclaved separately) | 2% (w/v) |

The pH was adjusted to 7.4

Kanamycin (25 mg/l) was added thereto. The pre-culture was incubated for 16 hours at 33° C. at 240 rpm on the shaker. A main culture was inoculated from this pre-culture, so that the initial OD (660 nm) of the main culture was 0.05. MM medium was used for the main culture.

| MM medium | |
|---|---|
| CSL (Corn Steep Liquor) | 5 g/l |
| MOPS (morpholinopropane sulfonic acid) | 20 g/l |
| Glucose (autoclaved separately) | 100 g/l |
| $(NH_4)_2SO4$ | 25 g/l |
| $KH_2PO_4$ | 0.1 g/l |
| $MgSO_4 * 7 H_2O$ | 1.0 g/l |
| $CaCl_2 * 2 H_2O$ | 10 mg/l |
| $FeSO_4 * 7 H_2O$ | 10 mg/l |
| $MnSO_4 * H_2O$ | 5.0 mg/l |
| Biotin (filter-sterilised) | 0.3 mg/l |
| Thiamine * HCl (filter-sterilised) | 0.2 mg/l |
| L-leucine (filter-sterilised) | 0.1 g/l |
| $CaCO_3$ | 25 g/l |

CSL, MOPS and the salt solution were adjusted to pH 7 with ammonia solution and autoclaved. The sterile substrate and vitamin solutions were then added, and the dry-autoclaved $CaCO_3$.

The culture was carried out in 10 ml volumes in a 100 ml Erlenmeyer flask with baffles. Kanamyin (25 mg/l) was added. The culture was carried out at 33° C. and at 80% air humidity.

After 48 hours and 72 hours the OD was determined at a measuring wavelength of 660 nm with the Biomek 1000 (Beckmann Instruments GmbH, Munich). The amount of lysine formed was determined with an amino acid analyser from Eppendorf-Biotronik (Hamburg, Germany) by ion exchange chromatography and post-column derivatisation with ninhydrin detection.

The result of the test is shown in Table 1.

TABLE 1

| Strain | OD (660 nm) | Lysine-HCl g/l |
|---|---|---|
| DSM5715/pEC-K18mob2 (48 hours) | 11.4 | 14.14 |
| DSM5715/pEC-K18mob2ptsHexp (48 hours) | 10.7 | 15.98 |
| DSM5715/pEC-K18mob2mob2 (72 hours) | 10.1 | 15.24 |
| DSM5715/pEC-K18mob2ptsHexp (72 hours) | 10.0 | 17.13 |

The abbreviations and names used have the following meaning:

| | |
|---|---|
| Kan: | resistance gene for kanamycin |
| Zeocin: | Zeocin resistance gene |
| ptsH: | ptsH gene from *C. glutamicum* |
| ColE1: | Replication origin of plasmid CelE1 |
| lacZ-alpha: | lacZ gene fragment from *E. coli* |
| lacZ-alpha': | fragment of the lacZ gene fragment from *E. coli* |
| per: | gene for controlling the copy number from pGA1 |
| oriV: | ColE1-like origin from pMB1 |
| rep: | plasmid-coded replication region from *C. glutamicum* plasmid pGA1 |
| RP4mob: | RP4 mobilisation site |
| EcoRI: | restriction site of the restriction enzyme EcoRI |
| HindIII: | restriction site of the restriction enzyme HindIII |
| KpnI: | restriction site of the restriction enzyme KpnI |
| XbaI: | restriction site of the restriction enzyme XbaI |

What is claimed is:

1. An isolated polynucleoride encoding a protein comprising the amino acid sequence of SEQ ID NO:2.

2. An isolated polynucleotide encoding a phosphocarrier component H polypeptide of a phosphotransferase system comprising an amino acid sequence that is at least 95% identical to that of SEQ ID NO:2.

3. An isolated polynucleotide comprising the nucleotide sequence of SEQ ID NO:1.

4. An isolated polynucleotide encoding a protein comprising the amino acid sequence of SEQ ID NO:4.

5. An isolated polynucleotide encoding a phosphocarrier component H polypeptide of a phosphotransferase system comprising an amino acid sequence that is at least 95% identical to that of SEQ ID NO:4.

6. isolated polynucleotide comprising the nucleotide sequence of SEQ ID NO:3.

7. A vector comprising a sequence identical to that of the isolated polynucleotide of any one of claims 1, 2, 3, 4, 5, and 6.

8. A bacterium transformed with the vector of claim 7.

* * * * *

SEQUENCE LISTING

```
<160> NUMBER OF SEQ ID NOS: 6

<210> SEQ ID NO 1
<211> LENGTH: 480
<212> TYPE: DNA
<213> ORGANISM: Corynebacterium glutamicum
<220> FEATURE:
<221> NAME/KEY: CDS
<222> LOCATION: (163)..(429)
<223> OTHER INFORMATION: ptsH wild-type gene

<400> SEQUENCE: 1
ggacattgtt tttgcttccg gtaacgtggc aaaacgaaca atgtctcact agactaaagt      60
gagatcgaca ttaaatcccc tcccttgggg ggtttaacta acaaatcgct gcgccctaat    120
ccgttcggat taacggcgta gcaacacgaa aggacacttt cc atg gct tcc aag       174
                                              Met Ala Ser Lys
                                                1 act gta acc gtc ggt tcc tcc gtt ggc ctg cac gca cgt cca gca tcc      222
Thr Val Thr Val Gly Ser Ser Val Gly Leu His Ala Arg Pro Ala Ser
  5                  10                  15                  20 atc atc gct gaa gcg gct gct gag tac gac gac gaa atc ttg ctg acc      270
Ile Ile Ala Glu Ala Ala Ala Glu Tyr Asp Asp Glu Ile Leu Leu Thr
                 25                  30                  35 ctg gtt ggc tcc gat gat gac gaa gag acc gac gcg tcc tct tcc ctc      318
Leu Val Gly Ser Asp Asp Asp Glu Glu Thr Asp Ala Ser Ser Ser Leu
             40                  45                  50 atg atc atg gcg ctg ggc gca gag cac ggc aac gaa gtt acc gtc acc      366
Met Ile Met Ala Leu Gly Ala Glu His Gly Asn Glu Val Thr Val Thr
         55                  60                  65 tcc gac aac gct gaa gct gtt gag aag atc gct gcg ctt atc gca cag      414
Ser Asp Asn Ala Glu Ala Val Glu Lys Ile Ala Ala Leu Ile Ala Gln
     70                  75                  80 gac ctt gac gct gag taaacaacgc tctgcttgtt aaaagctcgt tagaagcttg      469
Asp Leu Asp Ala Glu
 85 ttaaaagcgg t                                                          480
```

<210> SEQ ID NO 2
<211> LENGTH: 89
<212> TYPE: PRT
<213> ORGANISM: Corynebacterium glutamicum

<400> SEQUENCE: 2

Met Ala Ser Lys Thr Val Thr Val Gly Ser Ser Val Gly Leu His Ala
 1               5                  10                  15

Arg Pro Ala Ser Ile Ile Ala Glu Ala Ala Glu Tyr Asp Asp Glu
                20                  25                  30

Ile Leu Leu Thr Leu Val Gly Ser Asp Asp Asp Glu Glu Thr Asp Ala
            35                  40                  45

Ser Ser Ser Leu Met Ile Met Ala Leu Gly Ala Glu His Gly Asn Glu
    50                  55                  60

Val Thr Val Thr Ser Asp Asn Ala Glu Ala Val Glu Lys Ile Ala Ala
65                  70                  75                  80

Leu Ile Ala Gln Asp Leu Asp Ala Glu
                85

<210> SEQ ID NO 3
<211> LENGTH: 480
<212> TYPE: DNA
<213> ORGANISM: Corynebacterium glutamicum
<220> FEATURE:
<221> NAME/KEY: CDS
<222> LOCATION: (163)..(429)
<223> OTHER INFORMATION: ptsH allele

<400> SEQUENCE: 3
ggacattgtt tttgcttccg gtaacgtggc aaaacgaaca atgtctcact agactaaagt      60
gagatcgaca ttaaatcccc tcccttgggg ggtttaacta caaatcgct gcgccctaat     120 ccgttcggat taacggcgta gcaacacgaa aggacacttt cc atg gct tcc aag      174
                                                Met Ala Ser Lys
                                                 1 act gta acc gtc ggt tcc tcc gtt ggc ctg cac gca cgt cca gca tcc      222
Thr Val Thr Val Gly Ser Ser Val Gly Leu His Ala Arg Pro Ala Ser
 5                  10                  15                  20 atc atc gct gaa acg gct gct gag tac gac gac gaa atc ttg ctg acc      270
Ile Ile Ala Glu Thr Ala Ala Glu Tyr Asp Asp Glu Ile Leu Leu Thr
                25                  30                  35 ctg gtt ggc tcc gat gat gac gaa gag acc gac gcg tcc tct tcc ctc      318
Leu Val Gly Ser Asp Asp Asp Glu Glu Thr Asp Ala Ser Ser Ser Leu
            40                  45                  50 atg atc atg gcg ctg ggc gca gag cac ggc aac gaa gtt acc gtc acc      366
Met Ile Met Ala Leu Gly Ala Glu His Gly Asn Glu Val Thr Val Thr
    55                  60                  65 tcc gac aac gct gaa gct gtt gag aag atc gct gcg ctt atc gca cag      414
Ser Asp Asn Ala Glu Ala Val Glu Lys Ile Ala Ala Leu Ile Ala Gln
70                  75                  80 gac ctt gac gct gag taaacaacgc tctgcttgtt aaaagctcgt tagaagcttg      469
Asp Leu Asp Ala Glu
85 ttaaaagcgg t                                                         480

<210> SEQ ID NO 4
<211> LENGTH: 89
<212> TYPE: PRT
<213> ORGANISM: Corynebacterium glutamicum

<400> SEQUENCE: 4

-continued

```
Met Ala Ser Lys Thr Val Thr Val Gly Ser Ser Val Gly Leu His Ala
 1               5                  10                  15

Arg Pro Ala Ser Ile Ile Ala Glu Thr Ala Ala Glu Tyr Asp Asp Glu
                20                  25                  30

Ile Leu Leu Thr Leu Val Gly Ser Asp Asp Glu Glu Thr Asp Ala
            35                  40                  45

Ser Ser Ser Leu Met Ile Met Ala Leu Gly Ala Glu His Gly Asn Glu
        50                  55                  60

Val Thr Val Thr Ser Asp Asn Ala Glu Ala Val Glu Lys Ile Ala Ala
 65                 70                  75                  80

Leu Ile Ala Gln Asp Leu Asp Ala Glu
                85
```

<210> SEQ ID NO 5
<211> LENGTH: 20
<212> TYPE: DNA
<213> ORGANISM: Corynebacterium glutamicum
<220> FEATURE:
<223> OTHER INFORMATION: Primer ptsHexp1

<400> SEQUENCE: 5
accactggtg caatctccat                                           20

<210> SEQ ID NO 6
<211> LENGTH: 20
<212> TYPE: DNA
<213> ORGANISM: Corynebacterium glutamicum
<220> FEATURE:
<223> OTHER INFORMATION: Primer ptsHexp2

<400> SEQUENCE: 6
tttactcagc gtcaaggtcc                                           20